(12) United States Patent
Seifert et al.

(10) Patent No.: US 6,747,146 B2
(45) Date of Patent: Jun. 8, 2004

(54) METHOD OF PRODUCING NITROGUANIDINE- AND NITROENAMINE DERIVATIVES

(75) Inventors: Gottfried Seifert, Magden (CH); Thomas Rapold, Wallbach (CH); Verena Gisin, Ueken (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/325,559

(22) Filed: Dec. 20, 2002

(65) Prior Publication Data

US 2003/0092915 A1 May 15, 2003

Related U.S. Application Data

(63) Continuation of application No. 10/018,294, filed as application No. PCT/EP00/05762 on Jun. 21, 2000, now abandoned.

(30) Foreign Application Priority Data

Jun. 23, 1999 (CH) .............................................. 1171/99

(51) Int. Cl.$^7$ .................... C07D 273/04; C07D 403/12; C07D 417/12; C07D 401/12
(52) U.S. Cl. ..................... 544/67; 544/212; 546/270.7; 546/274.7; 546/330; 546/332; 548/205; 549/495
(58) Field of Search ................. 544/67, 212; 546/270.7, 546/274.7, 330, 332; 548/205; 549/495

(56) References Cited

U.S. PATENT DOCUMENTS

| 5,428,032 A | * | 6/1995 | Shiokawa et al. | ........ 514/226.8 |
| 6,187,487 B1 | * | 2/2001 | Matey et al. | ................ 514/245 |
| 6,376,487 B1 | * | 4/2002 | Maienfisch et al. | ...... 514/229.2 |

FOREIGN PATENT DOCUMENTS

JP          07 224062          8/1995

OTHER PUBLICATIONS

Zhou, Jingyao et al.: "Substitution reaction of dicyandiamide in the presence of phase transfer catalyst"; Chin. Sci. Bull. (1996), 41(5), pp. 1263–1265. STN Database accession No. 126:74527.

Gobel, Thomas et al.: "Synthetic approaches towards CGA 293'343: a novel broad–spectrum insecticide", Pestic. Sci., vol. 55, No. 3 (1999), pp. 355–357.

* cited by examiner

Primary Examiner—Peter O'Sullivan

(57) ABSTRACT

Method of producing compounds of formula

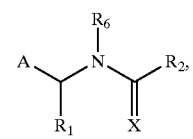

(I)

wherein $R_1$ is hydrogen or $C_1$–$C_4$-alkyl;

$R_2$ is hydrogen, $C_1$–$C_8$-alkyl, $C_3$–$C_6$-cycloalkyl, or a radical —$N(R_3)R_4$; or $R_2$ and $R_6$ together are —$CH_2$—$CH_2$—S—;

$R_3$ and $R_4$ are hydrogen, $C_1$–$C_4$-alkyl, $C_3$–$C_6$-cycloalkyl or a radical —$CH_2B$;

$R_6$ is hydrogen, $C_1$–$C_8$-alkyl, aryl or benzyl;

or $R_3$ and $R_6$ together are —$CH_2$—$CH_2$—, —$CH_2$—$CH_2$—$CH_2$—, —$CH_2$—O—$CH_2$—, —$CH_2$—S—$CH_2$— or —$CH_2$—$N(R_5)$—$CH_2$—;

X is CH—CN; CH—$NO_2$ or N—$NO_2$;

A is an optionally substituted, aromatic or non-aromatic, monocyclic or bicyclic heterocyclic radical; and B is optionally substituted phenyl, 3-pyridyl or thiazolyl;

characterised in that a compound of formula

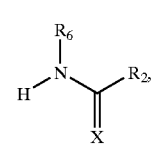

(II)

wherein $R_2$, $R_6$ and X have the same significance as given above in formula (I), is reacted in the presence of a phase transfer catalyst and a base with a compound of formula

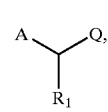

(III)

wherein A and $R_1$ have the same significance as given above in formula (I) and Q is a leaving group.

16 Claims, No Drawings

METHOD OF PRODUCING NITROGUANIDINE- AND NITROENAMINE DERIVATIVES

This application is a continuation of U.S. Ser. No. 10/018,294, filed Dec. 14, 2001, now abandoned, which is a 371 of PCT/EP00/05762, filed Jun. 21, 2000.

The present invention relates to a novel type of method of producing substituted 2-nitro-guanidine and nitroenamine derivatives.

It is known that in order to produce substituted nitroguanidines, nitroenamines or cyano-enamines, a further substituent may be introduced (e.g. by alkylation) into those compounds that may already be substituted once to several times (see e.g. EP patent application 0.375.907). Owing to the presence of several hydrogen atoms in the educts used as the starting material in these reactions, the previously proposed substitution reactions of this kind are often non-selective and lead to undesired substitution products. The afore-mentioned EP patent applications describe by way of example the production of 1,3-disubstituted 2-nitroguanidines by reacting monosubstituted nitroisothioureas with primary amines whilst cleaving mercaptan. However, these nitroisothiourea compounds, containing alkylthio leaving groups, which are proposed as starting compounds in the known processes, can only be obtained with difficulty. In EP-A-0-483.062, a process for the production of the compounds of formula (I) by hydrolysis of hexahydro-triazines is also described.

It has now been shown that the above-described methods of producing compounds of formula (I) do not satisfy the requirements demanded of a chemical production process, such as availability, toxicity, stability in storage and purity of the starting materials and excipients, reaction time, energy consumption and volumes yielded by the process, quantity and recovery of the accruing by-products and waste products, as well as purity and yield of the end product. There is therefore a need to provide improved methods of producing these compounds.

Accordingly, it is the aim of the present invention to provide an improved method of producing substituted 2-nitroguanidines, 2-nitroenamines, 2-cyanoenamines and 2-cyano-amines from readily obtainable starting compounds, which allows specific substitution without obtaining major amounts of undesired by-products.

Accordingly, the invention relates to a process for the preparation of compounds of formula

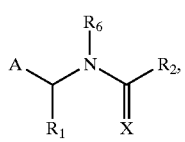

(I)

wherein
- $R_1$ is hydrogen or $C_1$–$C_4$-alkyl;
- $R_2$ is hydrogen, $C_1$–$C_8$-alkyl, $C_3$–$C_6$-cycloalkyl, or a radical —$N(R_3)R_4$; or $R_2$ and $R_6$ together are —$CH_2$—$CH_2$—$S$—, whereby the ethylene group is bonded to the nitrogen;
- $R_3$ and $R_4$, independently of one another, are hydrogen, $C_1$–$C_4$-alkyl, $C_3$–$C_6$-cycloalkyl or a radical —$CH_2B$;
- $R_6$ is hydrogen, $C_1$–$C_8$-alkyl, aryl or benzyl;
- or $R_3$ and $R_6$ together are —$CH_2$—$CH_2$—, —$CH_2$—$CH_2$—$CH_2$—, —$CH_2$—$O$—$CH_2$—, —$CH_2$—$S$—$CH_2$— or —$CH_2$—$N(R_5)$—$CH_2$—;

X is N—CN, CH—CN; CH—$NO_2$ or N—$NO_2$;

A is an aromatic or non-aromatic, monocyclic or bicyclic heterocyclic radical which is unsubstituted or—depending on the substitution possibilities of the ring system—mono- to penta-substituted by substituents selected from the group comprising halogen, $C_1$–$C_3$-alkyl, $C_1$–$C_3$-alkoxy, halogen-$C_1$–$C_3$-alkyl, $C_1$–$C_3$-halogenalkoxy, cyclopropyl, halogencyclopropyl, $C_2$–$C_3$-alkenyl, $C_2$–$C_3$-alkynyl, $C_2$–$C_3$-halogenalkenyl and $C_2$–$C_3$-halogenalkynyl, $C_1$–$C_3$-alkylthio, $C_1$–$C_3$-halogenalkylthio, allyloxy, propargyloxy, allylthio, propargylthio, halogenallyloxy, halogenallylthio, cyano and nitro; and B is phenyl, 3-pyridyl or thiazolyl, which are optionally substituted by one to three substituents from the group comprising $C_1$–$C_3$-alkyl, $C_1$–$C_3$-halogenalkyl, cyclopropyl, halo-gencyclopropyl, $C_2$–$C_3$-alkenyl, $C_2$–$C_3$-alkynyl, $C_1$–$C_3$-alkoxy, $C_2$–$C_3$-halogenalkenyl, $C_2$–$C_3$-halogenalkynyl, $C_1$–$C_3$-halogenalkoxy, $C_1$–$C_3$-alkylthio, $C_1$–$C_3$-halogenalkylthio, allyloxy, propargyloxy, allylthio, propargylthio, halogenallyloxy, halogenallylthio, halogen, cyano and nitro;

characterised in that a compound of formula

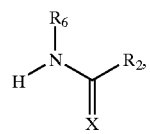

(II)

which is known or may be produced by methods known per se, and wherein $R_2$, $R_6$ and X have the same significance as indicated above for formula (I), is reacted in the presence of a phase transfer catalyst and a base with a compound of formula

(III)

which is known or may be produced by methods known per se, and wherein A and $R_1$ have the same significance as indicated above for formula (I) and Q is a leaving group.

The compounds of formula (I) may be present partly in the form of tautomers. Accordingly, any reference to compounds of formula (I) hereinbefore and hereinafter is understood to include also their corresponding tautomers, even if the latter are not specifically mentioned in each case.

The compounds of formula (I) and, where appropriate, the E/Z isomers and tautomers thereof, may be present as salts. Compounds of formula (I) having at least one basic centre may form e.g. acid addition salts. These are formed for example with strong inorganic acids, such as mineral acids, e.g. sulphuric acid, a phosphoric acid or a hydrohalic acid, with strong organic carboxylic acids, such as $C_1$–$C_4$alkanecarboxylic acids substituted where appropriate for example by halogen, e.g. acetic acid, such as optionally unsaturated dicarboxylic acids, e.g. oxalic, malonic, maleic, fumaric or phthalic acid, such as hydroxycarboxylic acids, e.g. ascorbic, lactic, malic, tartaric or citric acid, or benzoic acid, or with organic sulphonic acids, such as $C_1$–$C_4$alkanesulphonic or arylsulphonic acids substituted where appropriate for example by halogen, e.g. methanesulphonic or p-toluenesulphonic acid. Salts of compounds of formula (I) with acids of the said kind are preferably obtained when working up the reaction mixtures.

In a broader sense, compounds of formula (I) with at least one acid group can form salts with bases. Suitable salts with bases are for example metal salts, such as alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethylpropylamine, or a mono-, di- or trihydroxy-lower alkylamine, e.g. mono-, di- or triethanolamine. Corresponding internal salts where appropriate may also be formed. Preferred compounds within the scope of this invention are agrochemically advantageous salts. Hereinbefore and hereinafter, the free compounds of formula (I) are understood where appropriate to include also by analogy the corresponding salts, and the salts are understood to include also the free compounds of formula (I). The same applies to E/Z isomers and tautomers of compounds of formula (I) and salts thereof. The free form is preferred.

In the definition of formulae (I) to (III) given above and below, the individual generic terms are to be understood as follows:

Halogen signifies fluorine, chlorine, bromine and iodine, whereby fluorine, chlorine and bromine are preferred, especially chlorine. Halogen in this context is understood to be an independent substituent or part of a substituent, such as in halogenalkyl, halogenalkylthio, halogenalkoxy, halogencycloalkyl, halogenalkenyl, halogenalkinyl, halogenallyloxy or halogenallylthio. Alkyl, alkylthio, alkenyl, alkinyl and alkoxy radicals may be straight-chained or branched. If not defined otherwise, alkyl groups have up to 6 carbon atoms. Examples of such alkyls which may be mentioned are methyl, ethyl, propyl, isopropyl, butyl, isobutyl, sec.-butyl or tert.-butyl. Alkoxy radicals are for example methoxy, ethoxy, propoxy, isopropoxy or butoxy and the isomers thereof. Alkylthio is for example methylthio, ethylthio, isopropylthio, propylthio or the isomeric butylthio. Alkyl, alkoxy, alkenyl, alkinyl or cycloalkyl groups that are substituted by halogen can be only partly or also perhalogenated. The above-mentioned definitions apply here to halogen, alkyl and alkoxy. Examples of the alkyl elements of these groups are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; 2-chlorocyclopropyl or 2,2-difluoro-cyclopropyl; 2,2-difluorovinyl, 2,2-dichlorovinyl, 2-chloroalkyl, 2,3-dichlorovinyl or 2,3-dibromovinyl.

Typical representatives of alkenyl and alkinyl groups are allyl, methallyl, propargyl, vinyl and ethinyl. The double or triple bonds in allyloxy, propargyloxy, allylthio or propargylthio are separated from the connection point to the hetero atom (N, O or S) preferably by a saturated carbon atom.

If the defined alkyl, alkoxy, alkenyl, alkinyl or cycloalkyl groups are substituted by other substituents, they may be substituted once or many times by identical or different substituents from those listed. In the substituted groups, it is preferable for one or two further substituents to be present. Cycloalkyl is cyclopropyl, cyclobutyl, cyclopentyl or cyclohexyl.

Aryl signifies phenyl, naphthyl, phenanthrenyl or anthracenyl, especially phenyl.

In the context of the present invention, a heteroaryl radical preferably signifies a 5- to 7-membered, aromatic or non-aromatic ring with one to three hetero atoms selected from the group comprising N, O and S. Preference is given to aromatic 5- and 6-rings, which have a nitrogen atom as the hetero atom and optionally one further hetero atom, preferably nitrogen, oxygen or sulphur, especially nitrogen.

A leaving group Q is understood to be hereinbefore and hereinafter all the removable groups that are usual in chemical reactions and are known to the person skilled in the art; in particular halogens such as fluorine, chlorine, bromine, iodine, —O—C(=O)—A, —O—P(=O)(W)$_2$, —O—Si($C_1$–$C_8$-alkyl)$_3$, —O—($C_1$–$C_8$-alkyl), —O-aryl, —O—S(=O)$_2$W, —S—P(=O)(W)$_2$, —S—P(=S)(W)$_2$, —S—S—($C_1$–$C_8$-alkyl), —S—S-aryl, —S—($C_1$–$C_8$-alkyl), —S-aryl, —S(=O)W, or —S(=O)$_2$W, wherein W is optionally substituted $C_1$–$C_8$-alkyl, $C_2$–$C_8$-alkenyl, $C_2$–$C_8$-alkinyl, optionally substituted aryl, optionally substituted benzyl, $C_1$–$C_8$-alkoxy or di-($C_1$–$C_8$-alkyl)amine, in which the alkyl groups are independent of one another; NO$_3$, NO$_2$ or sulphate, sulphite, phosphate, phosphite, carboxylate, imino ester, N$_2$ or carbamate. Chlorine and bromine are especially preferred as the leaving group, particularly chlorine.

The compounds preferably produced in the process according to the invention are compounds of formula (I)

1) wherein R$_1$ is hydrogen;
2) wherein R$_2$ is a radical —N(R$_3$)R$_4$;
3) wherein R$_3$ is hydrogen or $C_1$–$C_4$-alkyl;
4) wherein R$_4$ is hydrogen;
5) wherein R$_2$ is a radical —N(R$_3$)R$_4$ and R$_3$ and R$_6$ together are —CH$_2$—CH$_2$—, —CH$_2$—O—CH$_2$— or —CH$_2$—N(CH$_3$)—CH$_2$—, especially —CH$_2$—CH$_2$— or —CH$_2$—O—CH$_2$—
6) wherein R$_6$ is hydrogen, $C_1$–$C_8$-alkyl, aryl or benzyl;
7) wherein X is CH—NO$_2$ or N—NO$_2$, especially N—NO$_2$;
8) wherein A is pyridyl thiazolyl or tetrahydrofuranyl, optionally substituted by halogen, $C_1$–$C_3$-alkyl, $C_1$–$C_3$-alkoxy, halogen-$C_1$–$C_3$-alkyl or $C_1$–$C_3$-halogenalkoxy; especially 2-chloro-thiazol-5-yl or 2-chloro-pyrid-5-yl.

The following individual compounds are most preferably produced by the process according to the invention:

Thiamethoxam of formula . . .

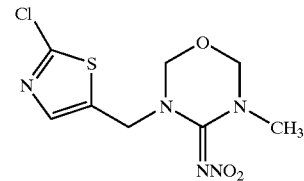

known from EP-A-580553;

Imidacloprid of formula

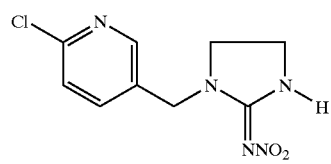

known from The Pesticide Manual, 11$^{th}$Ed. (1997), The British Crop Protection Council, London, page 706;

Acetamiprid (NI-25)

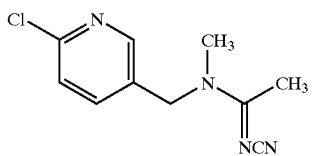

known from The Pesticide Manual, 11$^{th}$Ed. (1997), The British Crop Protection Council, London, page 9;

Nitenpyram (TI-304) of formula

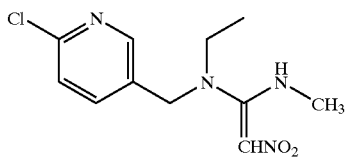

known from The Pesticide Manual, 11$^{th}$Ed. (1997), The British Crop Protection Council, London, page 880;

Clothianidin (Ti-435) of formula

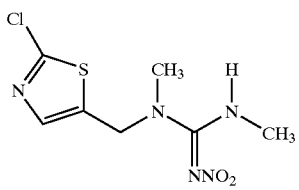

known from EP A 0 375907; and
MTI-446 of formula

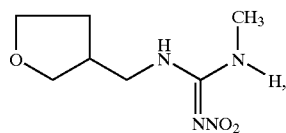

known from EP-0 649.845;
Thiacloprid of formula

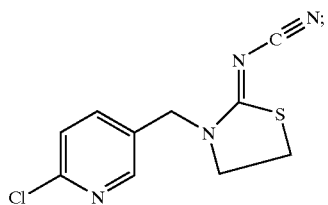

known from EP-A-192.060; and the compound of formula

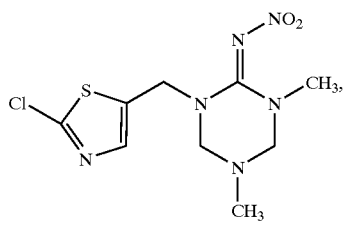

known from EP-0 428.941;

The phase transfer catalysts may be all customary compounds, i.e. quaternary ammonium salts, quaternary phosphonium salts, crown ethers, chelating agents, DABCO 1,4-diaza-bicyclo[2.2.2]octane and DBU (1,5-diazabicyclo [4.3.0]non-5-ene), and quaternary ammonium salts thereof; as well as polymeric phase transfer catalysts. They are listed in the paper "Phase Transfer Catalysts" by the company Fluka, Buchs, Switzerland, 1986 edition, pages 7 to 25. The phase transfer catalysts named therein are thus included by reference in the present invention.

Especially preferred quaternary ammonium salts as phase transfer catalysts are for example benzyltrimethyl ammonium chloride, benzyltriethyl ammonium chloride, benzyltributyl ammonium chloride, benzyltriethyl ammonium bromide, benzyltrimethyl ammonium methoxide, benzyltrimethyl ammonium hydroxide (triton B), glycidyl trimethyl ammonium chloride, hexadecyl-trimethyl ammonium chloride, hexadecyl-trimethyl ammonium bromide, hexadecyl-pyridinium bromide, hexadecyl-pyridinium chloride, 2-hydroxyethyl-trimethyl-ammonium chloride, 2-hydroxyethyl-trimethylammonium hydroxide, phenyltrimethyl-ammonium chloride, phenyltrimethyl ammonium hydroxide, tetrabutyl ammonium chloride, tetrabutyl ammonium bromide, tetrabutyl ammonium hydroxide, tetrabutyl ammonium tetrafluoroborate, tetrabutyl ammonium nitrate, tetradecyl ammonium chloride, tetradodecyl-ammonium acetate, tetraethyl ammonium chloride, tetraethyl ammonium hydroxide, tetradodecylammonium nitrate, tetradodecyl ammonium toluene sulphonate, tetrahexyl ammonium chloride, tetrahexylammonium bromide, tetramethyl ammonium chloride, tetramethyl-ammonium bromide, tetramethyl ammonium hydroxide, tetramethyl ammonium iodide, tetramethyl ammonium toluene sulphonate, tetraoctyl ammonium chloride, tetrapropyl ammonium chloride, tetrapropyl ammonium bromide, tributylmethyl ammonium chloride and tributylheptyl ammonium bromide, most preferably quaternary ammonium hydroxides, particularly tetramethyl ammonium hydroxide in the form of the pentahydrate.

The quaternary phosphonium salts may be benzyltriphenylphosphonium chloride, hexadecyltributylphosphonium bromide, hexadecyltrimethylphosphonium bromide, tetrabutylphosphonium chloride,tetraphenylphosphonium chloride or tetraphenylphosphonium bromide; or hexyltributylphosphonium bromide fixed to a polymeric matrix.

The crown ethers as phase transfer catalysts for the synthesis process according to the invention may be for example: 12-Crown-4, 15-Crown-5, 18-Crown-6, dibenzo-1 8-Crown-6; polyethylene glycols, for example with an average molecular weight of 1000, 1500 or 2000; tetraethylene glycol or tetraethylene glycol dimethylether.

Preferred solvents or diluents for carrying out the process according to the invention are esters, such as ethyl acetate; ethers, such as diethyl ether, dipropyl ether, diisopropyl ether, dibutyl ether, tert.-butylmethyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethyl-formamide, N,N-diethylformamide, N,N-dimethylacetamide, N-methylpyrrolidone or hexamethylphosphoric acid triamide; nitriles, such as acetonitrile or propionitrile; and sulphoxides, such as dimethyl sulphoxide; or water.

Especially preferred are esters of carbonic acid; acetic acid; formic acid; ketones; nitriles; ethers; N-alkylated acid amides; dimethyl sulphoxide; N-alkylpyrrolidones;

especially acetonitrile, dimethyl carbonate, diethyl carbonate, N-methylpyrrolidone, dimethylformamide, dimethyl acetamide, ethoxyethyl acetate, methyl acetate, propionitrile, butyronitrile, dimethyl sulphoxide, ethyl acetate, acetone, methyl ethyl ketone, methyl isobutyl ketone.

Particularly preferred solvents are acetonitrile, dimethyl carbonate, diethyl carbonate, N-methylpyrrolidone, dimethylformamide, dimethylacetamide and ethoxyethyl acetate, in particular dimethyl carbonate.

An especially preferred combination is dimethyl carbonate as the solvent with tetramethyl-ammonium hydroxide as the phase transfer catalyst.

The bases in water-free systems may be in particular carbonates, and in aqueous solvent systems also pH-controlled addition of alkali hydroxides; potassium carbonate is preferred. The amount of base employed is preferably one to two moles per mole of compound of formula (III).

The reaction is dependent on the boiling point of the solvent employed. An advantageous temperature range lies between ca. 40° C. and ca. 100° C., preferably between ca. 60° C. and ca. 70° C.

A reaction time of ca. 0.1 to ca. 24 hours is preferred, especially ca. 3 to ca. 5 hours.

It has now surprisingly been found that the process according to the invention is able to satisfy to a large extent the requirements listed initially, especially those relating to purity of the produced material.

In particular, it has been shown that, when carrying out the process according to the invention, the formation of undesired isomers can be suppressed. It has been shown especially in the case of the guanidine derivatives, that the substitution can also take place on the nitrogen which bears the nitro or cyano group:

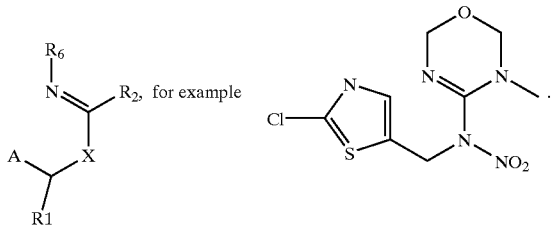

(IV)

The employment of suitable phase transfer catalysts permits the use of solvents, in which only small amounts of undesired isomers are obtained and which may be readily regenerated.

PREPARATION EXAMPLES

P1: Preparation of 5-(2-chlorothiazol-5-ylmethyl)-3-methyl-4-nitroimino-perhydro-1,3,5-oxadiazine (Thiamethoxam)

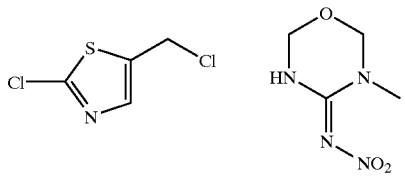

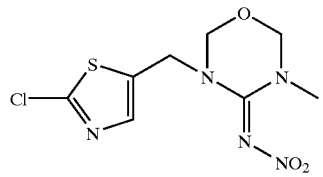

184 g of 100% 3-methyl-4-nitroimino-perhydro-1,3,5-oxadiazine in 400 g of dimethyl carbonate are placed in a sulphonation flask, and 168 g of 100% 2-chloro-5-chloromethyl-thiazole (1.0 moles) are added as a melt. This mixture is heated to 65° C. A mixture consisting of 350 g of dimethyl carbonate, 4 g of tetramethylammonium hydroxide pentahydrate and 242 g of potassium carbonate powder is measured in whilst stirring over 60 minutes at 62 to 68° C.

The reaction mixture is held for 5 to 6 hours whilst stirring vigorously, until more than 99% of the 2-chloro-5-chloromethylthiazole has reacted (LC control).

The reaction mixture is subsequently cooled to 45-50° C. and mixed with 600 g of water. The reaction mixture is adjusted to pH 6.5 with ca. 260 g of 32% hydrochloric acid and is then heated to 60 to 65° C. until everything dissolves. The solution is left to stand until phase separation takes place, and the organic phase is separated. The aqueous phase is reextracted at 50° C. with 300 g of dimethyl carbonate.

The organic phase from re-extraction is combined with the organic phase from the reaction mixture. The combined organic phases are concentrated under vacuum (350–400 mbar) at 60 to 65° C. to a final weight of 600 g (480 ml). The mixture is slowly cooled to 0–5° C. and held for 1 hour. Then the resulting suspension is filtered.

The filter cake is washed with 300 g of dimethyl carbonate of 5–10° C. in two portions and then with 300 ml of water in two portions, and the moist product is dried in a vacuum at 70° C.

Yield: 218–220 g of title product in a purity of 98 to 99% (74% of theory based on 100% 2-chloro-5-chloromethylthiazole). The above-mentioned isomer of formula (IV) is not found.

The title product may be obtained in a purity of 99.5% by recrystallisation from dimethyl carbonate.

An alternative preparation method comprises adding together the potassium carbonate, 3-methyl-4-nitroimino-perhydro-1,3,5-oxadiazine and the tetramethylammonium hydroxide pentahydrate in 1100 g of dimethyl carbonate, and measuring in the 2-chloro-5-chloromethylthiazole over 60 minutes at 65° C. The subsequent reaction and working up are then carried out as above.

We claim:

1. A process for the preparation of a compound of the formula

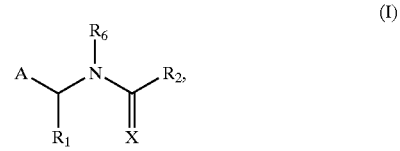

(I)

wherein $R_1$ is hydrogen or $C_1$–$C_4$-alkyl;

$R_6$ is hydrogen, $C_1$–$C_8$-alkyl, aryl or benzyl;

$R_2$ is hydrogen, $C_1$–$C_8$-alkyl, $C_3$–$C_6$-cycloalkyl, or a group of the formula —N($R_3$)$R_4$; or $R_2$ and $R_6$ together are a group —CH$_2$—CH$_2$—S—, the ethylene group of which is bonded to the nitrogen atom shown in the formula I;

$R_3$ and $R_4$, independently of one another, are hydrogen, $C_1$–$C_4$-alkyl, $C_3$–$C_6$-cycloalkyl or a group —$CH_2B$;

or $R_3$ and $R_8$ together are —$CH_2$—$CH_2$—, —$CH_2$—$CH_2$—$CH_2$—, —$CH_2$—O—$CH_2$—, —$CH_2$—S—$CH_2$— or —$CH_2$—N($R_5$)—$CH_2$—; $R_5$ is methyl;

X is N—CN, CH—CN, CH—$NO_2$ or N—$NO_2$;

A is an aromatic or non-aromatic, monocyclic or bicyclic, heterocyclic group, which is unsubstituted or—depending on the substitution possibilities of the ring system—mono- to penta-substituted by substituents, selected from the group consisting of halogen, $C_1$–$C_3$-alkyl, $C_1$–$C_3$-alkoxy, halogen-$C_1$–$C_3$-alkyl, halogen-$C_1$–$C_3$-alkoxy, cyclopropyl, halogencyclopropyl, $C_2$–$C_3$-alkenyl, $C_2$–$C_3$-alkynyl, halogen-$C_2$–$C_3$-alkenyl, halogen-$C_2$–$C_3$-alkynyl, $C_1$–$C_3$-alkylthio, halogen-$C_1$–$C_3$-alkylthio, allyloxy, propargyloxy, allylthio, propargylthio, halogenallyloxy, halogenallylthio, cyano and nitro; and B is a phenyl, 3-pyridyl or thiazolyl group which is optionally substituted by one to three substituents, selected from the group consisting of $C_1$–$C_3$-alkyl, halogen-$C_1$–$C_3$-alkyl, cyclopropyl, halogencyclopropyl, $C_2$–$C_3$-alkenyl, $C_2$–$C_3$-alkynyl, $C_1$–$C_3$-alkoxy, halogen-$C_2$–$C_3$-alkenyl, halogen-$C_2$–$C_3$-alkynyl, halogen-$C_1$–$C_3$-alkoxy, $C_1$–$C_3$-alkylthio, halogen-$C_1$–$C_3$-alkylthio, allyloxy, propargyloxy, allylthio, propargylthio, halogenallyloxy, halogenallylthio, halogen, cyano and nitro, which process is characterised in that a compound of the formula

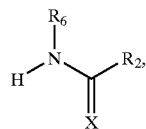

(II)

wherein $R_2$, $R_6$ and X are as defined hereinbefore for the formula I, is reacted in the presence of a solvent or diluent, of a phase transfer catalyst and of a base with a compound of the formula

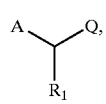

(III)

wherein A and $R_1$ are as defined hereinbefore for the formula I, and Q is a leaving group, the said solvent or diluent being an ester of carbonic acid.

2. A process according to claim 1, characterised in that the phase transfer catalyst employed is a quaternary ammonium salt.

3. A process according to claim 1, characterised in that the solvent or diluent employed is dimethyl carbonate or diethyl carbonate.

4. A process according to claim 1, characterised in that the base employed is a carbonate.

5. A process according to claim 1, characterised in that a compound of the formula I, wherein $R_2$ is a group of the formula —N($R_3$)$R_4$ and $R_3$ and $R_6$ together are —$CH_2$—$CH_2$—, —$CH_2$—O—$CH_2$—or —$CH_2N(CH_3)$—$CH_2$—, is prepared.

6. A process according to claim 1, characterised in that a compound of the formula I, wherein X is N—$NO_2$, is prepared.

7. A process according to claim 1, characterised in that a compound of the formula I, wherein A is a pyridyl, thiazolyl or tetrahydrofuranyl group, which is optionally substituted by halogen, $C_1$–$C_3$-alkyl, $C_1$–$C_3$-alkoxy, halogen-$C_1$–$C_3$-alkyl or halogen-$C_1$–$C_3$-alkoxy, is prepared.

8. A process according to claim 1, characterised in that the solvent or diluent employed is an ester of carbonic acid, the base employed is a carbonate and the phase transfer catalyst employed is a quaternary ammonium salt.

9. A process according to claim 3, characterised in that the solvent or diluent employed is dimethyl carbonate.

10. A process according to claim 4, characterised in that the base employed is potassium carbonate.

11. A process according to claim 5, characterised in that a compound of the formula I, wherein $R_2$ is a group of the formula —N($R_3$)$R_4$, $R_3$ and $R_6$ together are —$CH_2$—O—$CH_2$— and $R_4$ is methyl, is prepared.

12. A process according to claim 7, characterised in that a compound of the formula I, wherein A is 2-chlorothiazol-5-yl, is prepared.

13. A process according to claim 1, characterised in that the compound of the formula I, which is prepared, is thiamethoxam.

14. A process according to claim 2, characterised in that the phase transfer catalyst employed is tetramethyl ammonium chloride, tetramethyl ammonium bromide, tetramethyl ammonium hydroxide, tetramethyl ammonium iodide or tetramethyl ammonium toluene sulphonate.

15. A process according to claim 14, characterised in that the phase transfer catalyst is tetramethyl ammonium hydroxide.

16. A process according to claim 15, characterised in that the phase transfer catalyst is tetramethyl ammonium hydroxide in the form of the pentahydrate.

* * * * *